United States Patent [19]

Matsunaga et al.

[11] Patent Number: 4,755,262

[45] Date of Patent: Jul. 5, 1988

[54] METHOD FOR PURIFICATION OF GLYCIDYL ACRYLATE OR GLYCIDYL METHACRYLATE

[75] Inventors: Mitsumasa Matsunaga, Habikino; Yukio Tanaka, Nara; Akio Tani, Habikino; Shigeaki Matsumoto, Yamatokoriyama, all of Japan

[73] Assignee: Osaka Yuki Kagaku Kogyo Kabushiki Kaisha, Osaka, Japan

[21] Appl. No.: 112,306

[22] Filed: Oct. 26, 1987

[30] Foreign Application Priority Data

Apr. 13, 1987 [JP] Japan .................................. 62-88788

[51] Int. Cl.$^4$ ..................... B01D 3/34; C07D 301/27; C07D 301/36
[52] U.S. Cl. ........................................... 203/6; 203/8; 203/33; 203/34; 203/DIG. 21; 549/515; 549/557; 549/202
[58] Field of Search ..................... 203/6, 8, 29, 33, 34, 203/35, 50, DIG. 21; 549/515, 557, 202

[56] References Cited

U.S. PATENT DOCUMENTS

| 2,537,981 | 1/1951 | Edwards | 549/515 |
| 2,556,075 | 6/1951 | Erickson | 549/515 |
| 3,053,855 | 9/1962 | Maerker et al. | 549/515 |
| 3,372,142 | 3/1968 | Smith | 549/515 |
| 3,661,938 | 5/1972 | Heilman | 549/515 |
| 4,624,975 | 11/1986 | Pham | 549/202 |

FOREIGN PATENT DOCUMENTS

| 45-17661 | 6/1970 | Japan | 549/202 |
| 47-41884 | 10/1972 | Japan | 549/202 |

OTHER PUBLICATIONS

Chemical Abstracts, vol. 104, No. 19, May 12, 1986, Abstr. No. 168,45/n, 5/12/86, Shimizu, Y. et al., Jpn Kokai 85/208,974, Oct. 21, 1985.

Primary Examiner—Wilbur Bascomb
Attorney, Agent, or Firm—Armstrong, Nikaido, Marmelstein & Kubovcik

[57] ABSTRACT

This invention relates to a method for the purification of glycidyl acrylate or glycidyl methacrylate. Specifically, the invention effects the purification by using a residual catalyst-inactivating additive and consequently produces highly purified glycidyl acrylate or glycidyl methacrylate containing substantially no epichlorohydrin and having a low chlorine content.

1 Claim, No Drawings

METHOD FOR PURIFICATION OF GLYCIDYL ACRYLATE OR GLYCIDYL METHACRYLATE

BACKGROUND OF THE INVENTION

It has been known to the art that glycidyl acrylate or glycidyl methacrylate (hereinafter referred to collectively as "glycidyl (meth)acrylate") is synthesized by causing an alkali metal salt of acrylic acid or methacrylic acid (hereinafter referred to collectively as "(meth)acrylic acid") and epichlorohydrin of an amount in the range of 3 to 10 mols per mol of the aforementioned alkali metal salt to react with each other in the presence of about 0.3 to 2.0 mol% of a quaternary ammonium salt as a catalyst and about 0.01 to 0.2 wt% of a polymerization inhibitor, both based on the amount of the aforementioned alkali metal salt of (meth)acrylic acid, at a temperature in the range of 80° to 120° C. for a period in the range of 1 to 5 hours. The crude glycidyl (meth)acrylate obtained consequently is filtered or washed with water to remove therefrom an alkali metal chloride occurring as a by-product of the reaction, then distilled to expel therefrom any excess of epichlorohydrin, and finally purified by vacuum distillation to become a finished product.

In the glycidyl (meth)acrylate thus obtained as a finished product, however, epichlorohydrin still persists in a concentration approximately in the range of 0.1 to 1.0% by weight, with the inevitable result that the purity of glycidyl (meth)acrylate is lowered and the content of free chlorine is increased. Such is the true state of affairs. Since glycidyl (meth)acrylate is mainly used as a raw material for coating materials and results, the aforementioned increase of the free chlorine content results in acceleration of the corrosion of coated metallic substrates and loss of the economic worth of glycidyl (meth)acrylate. Further, epichlorohydrin possesses toxicity manifested in the form of violent stimulation of the skin. The glycidyl (meth)acrylate which contains this toxic compound demands particularly meticulous care to be exercised during the handling thereof. Thus, it has room for further improvement from the standpoints of safety, hygiene, and ecology.

Heretofore, as regards methods for the purification of glycidyl (meth)acrylate, various proposals have been made which are mainly aimed at heightening the yield of purification. For example:

(1) A method which converts the reaction mixture into a finished product by adding water to the reaction mixture, hydrolyzing the resultant mixture, and then distilling the organic phase separated in consequence of the hydrolysis (as disclosed in Japanese Patent Publication No. 28762/1970.

(2) A method which promotes stabilization of glycidyl (meth)acrylate resulting from the reaction by the addition thereto of either a sulfonate, an alkyl sulfuric ester or a sulfonate-form cation-exchange resin (as disclosed in Japanese Patent Application Laid-open No. 72115/1973), and (3) A method which promotes stabilization of glycidyl (meth)acrylate resulting from the reaction by the addition thereto of either an alkali metal salt of mono- or di-nitrophenol or an alkali metal salt of a mono-, di-, or tri-nitrobenzoic acid (as disclosed in Japanese Patent Publication No. 42075/1982) have been introduced to the art.

These prior publications made absolutely no mention of a process for the production of glycidyl (meth)acrylate containing substantially no epichlorohydrin. The inventions disclosed thereby have objects entirely different from those of the present invention.

As means of producing glycidyl (meth)acrylate without use of epichlorohydrin, methods resorting to transesterification of methyl acrylate or methyl methacrylate with glycidol have been proposed (as disclosed in Japanese Patent Application Laid-open No. 15420/1975, Japanese Patent Publication No. 6133/1978, Japanese Patent Publication No. 38421/1972, French Pat. No. 2,088,971, Japanese Patent Application Laid-open No. 25174/1977, Japanese Patent Application Laid-open No. 3007/1979, and Japanese Patent Application Laid-open No. 118075/1981).

Since glycidol as the starting material possesses poor shelf life and undergoes degradation of purity with elapse of time even at room temperature, these methods are not suitable for stable production of glycidyl (meth)acrylate on a commercial scale.

As another conceivable method, precision distillation of the ordinary product may attain in some measure the same primary object as contemplated by the present invention. This method, however, is unfit for mass production of the compound on a commercial scale because the application of heat required for the distillation not merely lowers the yield heavily but also entails a serious economic loss.

BRIEF SUMMARY OF THE INVENTION

This invention aims to produce glycidyl (meth)acrylate of high purity possessing a low chlorine content by lowering the residual epichlorohydrin content to a level of not more than 0.01% by weight based on the weight of the glycidyl (meth)acrylate as a finished product.

To be specific, this invention accomplishes the object described above by adding to the crude glycidyl (meth)acrylate a specific compound as a residual catalyst-inactivating additive thereby treating the crude compound and separating the refined compound by distillation.

DETAILED DESCRIPTION OF THE INVENTION

It has been ascertained to the inventors that even when glycidyl (meth)acrylate is produced by causing an alkali metal salt of (meth)acrylic acid to react with epichlorohydrin in the presence of a quaternary ammonium salt as a catalyst, filtering the resultant reaction mixture thereby removing therefrom the alkali metal chloride by-produced in the reaction, and continuing expulsion of excess epichlorohydrin through distillation for concentration of the reaction product, the epichlorohydrin cannot be completely eliminated from the concentrate, with the result that the finally produced glycidyl (meth)acrylate has an epichlorohydrin content in the range of 0.1 to 1.0% by weight. After a continued study in search of the cause for the persistence of this impurity, the inventors have found that as indicated in Table 1, the quaternary ammonium salt serving as a catalyst for the reaction is not thoroughly removed by filtration but is suffered to remain in a minute amount and accelerate remarkably a new reaction productive of epichlorohydrin during the expulsion through distillation of epichlorohydrin from 1,3-dichloro-2-propanol which is readily formed as a by-product of the reaction from epichlorohydrin, the alkali metal chloride, and a minute amount of water.

In an experiment, when a solution consisting of 5% by weight of 1,3-dichloro-2-propanol containing 50 ppm of hydroquinone monomethyl ether as a polymerization inhibitor and 95% by weight of glycidyl methacrylate was mixed with a quaternary ammonium salt and the resultant mixture was heated to a temperature in the range of 90° to 100° C., there ensued ready formation of epichlorohydrin.

TABLE 1

| Ester | Quaternary ammonium salt | | Heating conditions | | Analyses (% by weight) | |
|---|---|---|---|---|---|---|
| | Name | Amount used (%) | Temp. (°C.) | Time (hr) | ECH | DCH |
| Glycidyl methacrylate | — | — | 90~100 | 6 | 0 | 5 |
| Glycidyl methacrylate | Tetramethyl ammonium chloride | 0.02 | 90~100 | 6 | 2.8 | 2.2 |
| Glycidyl methacrylate | Tetraethyl ammonium chloride | 0.02 | 90~100 | 6 | 2.7 | 2.3 |
| Glycidyl methacrylate | Triethylbenzyl ammonium chloride | 0.02 | 90~100 | 6 | 3.3 | 1.7 |
| Glycidyl methacrylate | Trimethylbenzyl ammonium chloride | 0.02 | 90~100 | 6 | 3.2 | 1.8 |

(Note)
ECH = Epichlorohydrin,
DCH = 1,3-dichloro-2-propanol.

After a continued study in search of a way of inactivating the quaternary ammonium salt, the inventors have found that a heteropoly acid or an alkali metal salt of the heteropoly acid represented by the general formula (I):

$$Z_m XY_{12} O_{40} \cdot nH_2O \quad (I)$$

(wherein X stands for a phosphorous or silicon atom, Y for a tungsten or molybdenum atom, Z for a hydrogen atom or an alkali metal atom selected from among lithium, sodium, and potassium, m for 3 where X denotes a phosphorus atom or 4 where X denotes a silicon atom, and n for a positive integer in the range of 0 to 30) is capable of effecting the inactivation. This invention has been perfected as the result.

To be specific, this invention is directed to a method for purification of the crude glycidyl (meth)acrylate obtained by the reaction of an alkali metal salt of (meth)acrylic acid with epichlorohydrin in the presence of a quaternary ammonium salt catalyst to an extent such as to lower the epichlorohydrin content thereto to a practically negligible level, i.e. to not more than 0.01% by weight, which method is characterized by the steps of adding at least either a heteropoly acid represented by the general formula (I) or an alkali metal salt of the heteropoly acid to the crude glycidyl (meth)acrylate thereby treating the crude product therewith and subsequently isolating the purified product through distillation.

In the present invention, the heteropoly acid or the alkali metal salt thereof represented by the general formula (I) readily reacts with the quaternary ammonium salt and gives rise to removal of halogenated hydrogen or halogenated alkali metal salt and induces formation of a stable complex salt, with the result that the quaternary ammonium salt is inactivated and the occurrence of epichlorohydrin from 1,3-dichloro-2-propanol is precluded.

Desirable examples of the heteropoly acid or the alkali metal salt of the heteropoly acid represented by the general formula (I) include phosphotungstic acid, lithium phosphotungstate, sodium phosphotungstate, potassium phosphotungstate, silicotungstic acid, lithium silicotungstate, sodium silicotungstate, potassium silicotungstate, phosphomolybdic acid, lithium phosphomolybdate, sodium phosphomolybdate, potassium phosphomolybdate, silicomolybdic acid, lithium silicamolybdate, sodium silicomolybdate, and potassium silicomolybdate.

This additive is used in an amount approximately in the range of 1 to 5 mol%, preferably 1 to 2 mol%, based on the amount of the quaternary ammonium salt used as a catalyst for the reaction. The addition of this additive is desired to be made after the removal of the halogenated alkali metal salt which follows the completion of the reaction. The desired treatment of the crude glycidyl (meth)acrylate with the additive is effected by stirring the resultant mixture for a period of 0.5 to 1 hour following the addition. During the subsequent course of the isolation through distillation, the aforementioned treatment with the additive manifests an effect of precluding the formation of epichlorohydrin from 1,3-dichloro-2-prophanol without interfering with the effect of inhibiting polymerization to be brought about by a separately added polymerization inhibitor.

The reaction of the present invention is effected by the conventional procedure which comprises synthesizing an alkali metal salt of (meth)acrylic acid by the neutralization of (meth)acrylic acid with an alkali metal compound and subsequently adding epichlorohydrin, a quaternary ammonium salt, and a catalyst to the alkali metal salt thereby allowing the reaction to proceed.

Generally, the alkali metal salt of (meth)acrylic acid to be used herein is in the form of a sodium salt or potassium salt. This salt can be easily synthesized by the reaction of (meta)acrylic acid with an alkali metal compound such as, for example, sodium hydroxide or potassium hydroxide.

Desirable examples of the quaternary ammonium salt to be used as a catalyst herein include tetramethyl ammonium chloride, tetraethyl ammonium chloride, trimethylbenzyl ammonium chloride, and triethylbenzyl ammonium chloride.

Examples of the polymerization inhibitor to be advantageously used herein include phenothiazine, hydroquinone, hydroquinone monomethyl ether, and N,N'-diphenyl paraphenylene diamine.

The method of the present invention can be carried out generally in the absence of a solvent. Optionally, it can be carried out in the presence of an organic solvent containing no halogen element. This invention does not discriminate this organic solvent on account of the choice among the nonpolar, polar, and azeotropic species.

EXAMPLE 1

Sodium methacrylate was synthesized by the neutralization of 119.5 g (1.389 mols) of methacrylic acid with 55.5 g (1.389 mols) of sodium hydroxide. A mixture consisting of 150.0 g of substantially anhydrous sodium methacrylate obtained by dehydrating the product of the neutralization and 642.4 g (6.945 mols) of epichlorohydrin was placed in a flask provided with a stirrer, a thermometer, and a reflux condenser. Then, 0.76 g (0.007 mol) of tetramethyl ammonium chloride and 0.4 g (0.002 mol) of phenothiazine were added to the contents of the flask. The resultant contents of the flask were stirred at 90° C. for three hours in induce reaction. After the reaction was completed, sodium chloride by-produced by the reaction was separated by filtration. The filtrate and 0.28 g (0.0001 mol) of a 26-30-hydrate of phosphotungstic acid added thereto were stirred at 65° C. for 0.5 hour and then distilled under a vacuum of 50 to 70 mmHg to expel 488 g of unaltered epichlorohydrin. The residue of this distillation was placed in an 5-shelf distillation column and distilled therein at the bottoms temperature in the range of 80° to 85° C. Consequently, 193.3 g of glycidyl methacrylate as a fraction distilling at 65° to 66° C./3 mmHg. This fraction, by quantitative gas chromatography, was found to have glycidyl methacrylate content of 98.6% and an epichlorohydrin content of 0.0021%.

COMPARATIVE EXPERIMENT 1

The procedure of Example 1 was repeated to effect the reaction of sodium methacrylate with epichlorohydrin and subsequent removal of the by-produced sodium chloride. Then, the resultant reaction mixture was distilled by following the procedure of Example 1, excepting the addition of phosphotungstic acid was omitted. Consequently, there was obtained 157.6 g of a fraction having a glycidyl methacrylate content of 97.7% and a epichlorohydrin content of 0.42%.

EXAMPLES 2 THROUGH 12 AND COMPARATIVE EXPERIMENTS 2 THROUGH 4

By following the procedure of Example 1, sodium acrylate or sodium methacrylate synthesized by the reaction of acrylic acid or methacrylic acid with sodium hydroxide was allowed to react with epichlorohydrin in the presence of a varying catalyst indicated in Table 2. The reaction was carried out at a temperature in the range of 90° to 100° C. for a period in the range of 2 to 4 hours, invariably in the presence of 0.4 g of phenothiazine as a polymerization inhibitor.

After the reaction was completed, the reaction mixture was filtered to remove therefrom sodium chloride. Then, in the presence of a varying additive indicated in the table, the residue of the filtration was distilled under a vacuum of 50 to 80 mmHg to expel epichlorohydrin and then further distilled under a vacuum of 3 to 5 mmHg. The results are shown in Table 2.

In Comparative Experiments 2 through 4, reaction and purification were carried out by following the foregoing procedure, excepting the use of an additive was omitted. The results were additionally shown in Table 2.

TABLE 2

| | | Acrylic acid or methacrylic acid | Amount of sodium hydroxide used (g) | Amount of epichlorohydrin used (g) | Catalyst | | Additive (Note) | |
|---|---|---|---|---|---|---|---|---|
| | | Name / Amount used (g) | | | Name | Amount used (g) | Name | Amount used (g) |
| Example | 2 | M.A.* 119.5 | 55.5 | 642.4 | Triethylbenzyl ammonium chloride | 1.59 | Phosphotungstic acid | 0.28 |
| | 3 | M.A.* 119.5 | 55.5 | 642.4 | Tetramethyl ammonium chloride | 0.76 | Silicotungstic acid | 0.28 |
| | 4 | M.A.* 119.5 | 55.5 | 642.4 | Tetramethyl ammonium chloride | 0.76 | Phosphomolybdic acid | 0.18 |
| | 5 | M.A.* 119.5 | 55.5 | 642.4 | Tetramethyl ammonium chloride | 0.76 | Silicomolybdic acid | 0.18 |
| | 6 | M.A.* 119.5 | 55.5 | 642.4 | Tetramethyl ammonium chloride | 0.76 | Sodium phosphotungstate | 0.29 |
| | 7 | M.A.* 119.5 | 55.5 | 642.4 | Tetramethyl ammonium chloride | 0.76 | Sodium silicotungstate | 0.29 |
| | 8 | A.A.** 100 | 55.5 | 642.4 | Tetramethyl ammonium chloride | 0.76 | Phosphotungstic acid | 0.28 |
| | 9 | A.A.** 100 | 55.5 | 642.4 | Triethylbenzyl ammonium chloride | 1.59 | Phosphotungstic acid | 0.28 |
| | 10 | A.A.** 100 | 55.5 | 642.4 | Tetramethyl ammonium chloride | 0.76 | Sodium phosphotungstate | 0.29 |
| | 11 | M.A.* 119.5 | 55.5 | 642.4 | Tetramethyl ammonium chloride | 0.76 | Lithium phosphotungstate | 0.29 |
| | 12 | M.A.* 119.5 | 55.5 | 642.4 | Tetramethyl ammonium chloride | 0.76 | Potassium phosphotungstate | 0.30 |
| C.E.*** | 2 | M.A.* 119.5 | 55.5 | 642.4 | Triethylbenzyl ammonium chloride | 1.59 | — | — |
| | 3 | A.A.* 100 | 55.5 | 642.4 | Tetramethyl ammonium chloride | 0.76 | — | — |
| | 4 | A.A.* 100 | 55.5 | 642.4 | Triethylbenzyl ammonium chloride | 1.59 | — | — |

| | | Yield of glycidyl acrylate or glycidyl methacrylate (g) | Purity of glycidyl acrylate or glycidyl methacrylate (%) | Epichlorohydrin content of product (%) |
|---|---|---|---|---|
| Example | 2 | 192.8 | 98.5 | 0.0033 |
| | 3 | 192.3 | 98.5 | 0.0028 |
| | 4 | 192.5 | 98.3 | 0.0035 |
| | 5 | 192.5 | 98.4 | 0.0031 |

TABLE 2-continued

|   |   |   | | |
|---|---|---|---|---|
|   | 6 | 190.7 | 98.2 | 0.0045 |
|   | 7 | 190.4 | 98.1 | 0.0046 |
|   | 8 | 156.8 | 98.2 | 0.0026 |
|   | 9 | 156.5 | 97.9 | 0.0037 |
|   | 10 | 151.1 | 97.7 | 0.0065 |
|   | 11 | 190.3 | 98.0 | 0.0050 |
|   | 12 | 190.6 | 98.2 | 0.0048 |
| C.E.*** | 2 | 147.9 | 97.5 | 0.66 |
|   | 3 | 115.6 | 97.1 | 0.58 |
|   | 4 | 108.5 | 97.0 | 0.79 |

*M.A. = Methacrylic acid
**A.A. = Acrylic acid
***C.E. = Comparative Experiment
(Note)
The amounts of heteropoly acid or an alkali metal salt thereof indicated above used herein are those including the amounts of 26–30 molecules of water of crystallization per mol.

What is claimed is:

1. A method for the purification of crude glycidyl acrylate or crude glycidyl methacrylate obtained by the reaction of an alkali metal of acrylic acid or methacrylic acid with epichlorohydrin in the presence of a quaternary ammonium salt as a catalyst, which method is characterized by the steps of adding to said crude glycidyl acrylate or crude glycidyl methacrylate at least one member selected from the group consisting of heteropoly acids or alkali metal salts thereof represented by the general formula:

$$Z_m XY_{12}O_{40} \cdot nH_2O$$

(wherein X stands for a phosphorus or silicon atom, Y for a tungsten or molybdenum atom, Z for a hydrogen atom or an alkali metal atom selected from among lithium, sodium, and potassium, m for 3 where X denotes a phosphorus atom or 4 where X denotes a silicon atom, and n for a positive integer in the range of 0 to 30) thereby effecting treatment of said crude glycidyl acrylate or crude glycidyl methacrylate and subsequently separating consequently purified glycidyl acrylate or glycidyl methacrylate by distillation.

* * * * *